(12) United States Patent
Tripp et al.

(10) Patent No.: US 8,436,168 B2
(45) Date of Patent: May 7, 2013

(54) METHODS OF MAKING HIV ATTACHMENT INHIBITOR PRODRUG COMPOUND AND INTERMEDIATES

(75) Inventors: Jonathan Clive Tripp, Westfield, NJ (US); Dayne Dustan Fanfair, East Windsor, NJ (US); Mitchell J. Schultz, Decatur, IL (US); Saravanababu Murugesan, Edison, NJ (US); Richard J. Fox, Yardley, PA (US); Chung-Pin H. Chen, Madison, CT (US); Sabrina E. Ivy, East Brunswick, NJ (US); Joseph Francis Payack, Somerset, NJ (US); Wendel W. Doubleday, Snohomish, WA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 13/359,708

(22) Filed: Jan. 27, 2012

(65) Prior Publication Data

US 2013/0030178 A1   Jan. 31, 2013

Related U.S. Application Data

(60) Provisional application No. 61/437,821, filed on Jan. 31, 2011.

(51) Int. Cl.
*C07F 9/6561* (2006.01)

(52) U.S. Cl.
USPC .......................................................... 544/337

(58) Field of Classification Search ................... 544/337
See application file for complete search history.

(56) References Cited

U.S. PATENT DOCUMENTS

| 7,354,924 | B2 | 4/2008 | Wang et al. |
| 7,601,715 | B2 | 10/2009 | Soundararajan et al. |
| 7,745,625 | B2 | 6/2010 | Ueda et al. |
| 7,776,863 | B2 | 8/2010 | Lin et al. |

*Primary Examiner* — Kristin Bianchi
(74) *Attorney, Agent, or Firm* — John F. Levis

(57) ABSTRACT

A method for making the compound of Formula I:

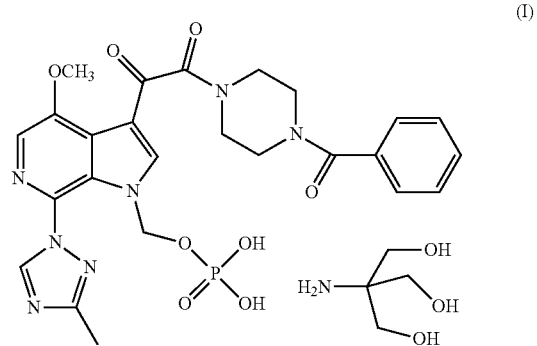

is set forth using alkylation, amidation, chlorination and phosphate installation procedures.

21 Claims, No Drawings

METHODS OF MAKING HIV ATTACHMENT INHIBITOR PRODRUG COMPOUND AND INTERMEDIATES

CROSS REFERENCE TO RELATED APPLICATIONS

This non-provisional application claims the benefit of U.S. Provisional Application Ser. No. 61/437,821 filed Jan. 31, 2011.

FIELD OF THE INVENTION

The invention relates to methods of making prodrug compounds useful against HIV, and in particular, to methods of making the prodrug 1-benzoyl-4-[2-[4-methoxy-7-(3-methyl-1H-1,2,4-triazol-1-yl)-1-[(phosphonooxy)methyl]-1H-pyrrolo[2,3-c]pyridin-3-yl]-1,2-dioxoethyl]-piperazine, as well certain intermediates thereof, using novel alkylation, amidation, chlorination, and phosphate installation strategies. The invention also relates to the compounds obtained by the processes herein set forth.

BACKGROUND OF THE INVENTION

The HIV attachment inhibitor prodrug compound identified as 1-benzoyl-4-[2-[4-methoxy-7-(3-methyl-1H-1,2,4-triazol-1-yl)-1-[(phosphonooxy)methyl]-1H-pyrrolo[2,3-c]pyridin-3-yl]-1,2-dioxoethyl]-piperazine, and having the structural formula:

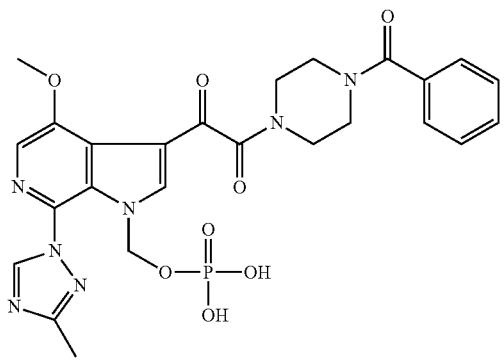 [SMILES: COc1cnc(-n2cnc(C)n2)c2c1c(C(=O)C(=O)N1CCN(C(=O)c3ccccc3)CC1)cn2COP(=O)(O)O]

has been set forth and described in U.S. Pat. No. 7,745,625, which is incorporated herein in its entirety. This compound is the phosphate prodrug of the basic compound having the structural formula:

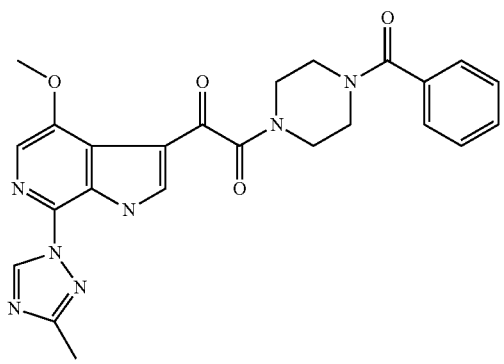 [SMILES: COc1cnc(-n2cnc(C)n2)c2[nH]cc(C(=O)C(=O)N3CCN(C(=O)c4ccccc4)CC3)c12]

which is set forth and described in U.S. Pat. No. 7,354,924, also incorporated herein in its entirety. Both this compound and the prodrug identified above have so far demonstrated excellent prowess against HIV.

During scale-up procedures for the production of the phosphate prodrug compound, two compounds were utilized in an alkylation process between phosphonic acid, P-(chloromethyl)-, bis(1,1-dimethylethyl) ester and 1-(4-benzoylpiperazin-1-yl)-2-(4-methoxy-7-(3-methyl-1H-1,2,4-triazol-1-yl)-1H-pyrrolo[2,3-c]pyridin-3-yl)ethane-1,2-dione.

However, these compounds have proved to be difficult to process, or unstable and difficult to procure on scale. Furthermore, the yields of the alkylation reaction using these compounds has diminished as the reaction was scaled up.

What is now needed in the art are new processes for making the HIV prodrug compound 1-benzoyl-4-[2-[4-methoxy-7-(3-methyl-1H-1,2,4-triazol-1-yl)-1-[(phosphonooxy)methyl]-1H-pyrrolo[2,3-c]pyridin-3-yl]-1,2-dioxoethyl]-piperazine, as well as intermediate compounds. These new processes should utilize distinct alkylation, amidation, chlorination and phosphate installation procedures. Also needed are new compounds and intermediates which are generated as a result of the novel processes.

SUMMARY OF THE INVENTION

In a first embodiment, the invention provides a method for making the compound of Formula I:

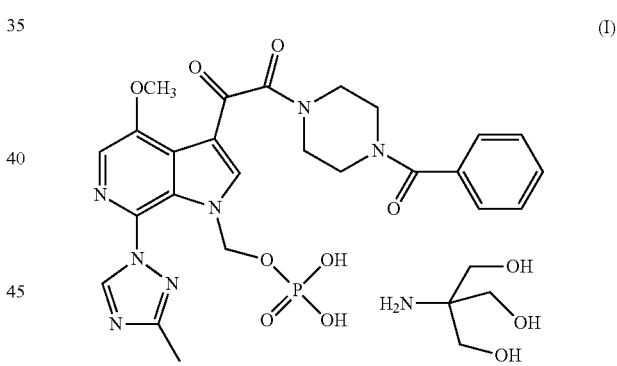

(I)

with the chemical name 2-amino-2-(hydroxymethyl)propane-1,3-diol-(3-(2-(4-benzoylpiperazin-1-yl)-2-oxoacetyl)-4-methoxy-7-(3-methyl-1H-1,2,4-triazol-1-yl)-1H-pyrrolo[2,3-c]pyridin-1-yl)methyl phosphate which comprises:

(a) brominating the compound

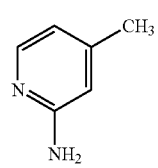

(1)

to yield the compound

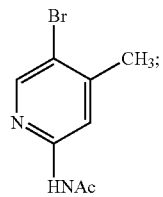 (2)

and
(b) nitrating compound 2 to yield the compound

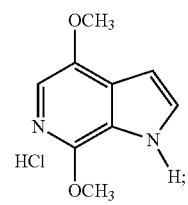 (3)

and
(c) converting the amine group on compound 3 to a methoxy group to yield compound (4)

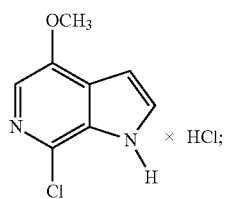

and
(d) then converting compound 4 to the compound (5)

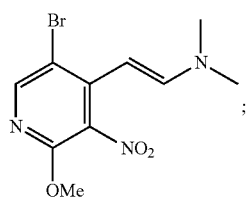

and
(e) converting compound 5 to the compound (6)

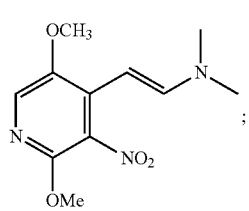

and
(f) forming a bicyclic structure from compound 6 to yield

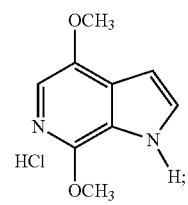 (7)

and
(g) then chlorinating compound 7 to produce

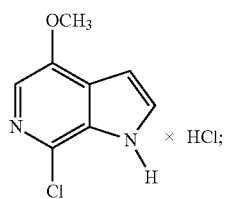 (8)

and
(h) thereafter adding a triazolyl moiety to the compound 8 to yield

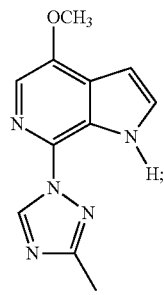 (9)

and
(i) converting compound 9 to the structure

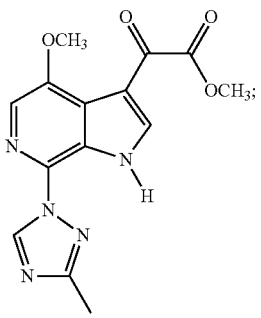 (10)

and (j) modifying compound 10 to yield the compound (11)

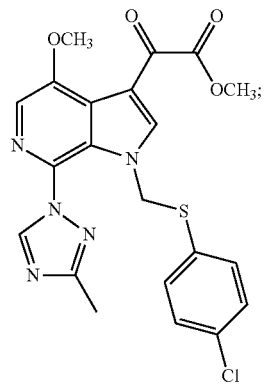

and (k) reacting compound 11 to produce the compound (12)

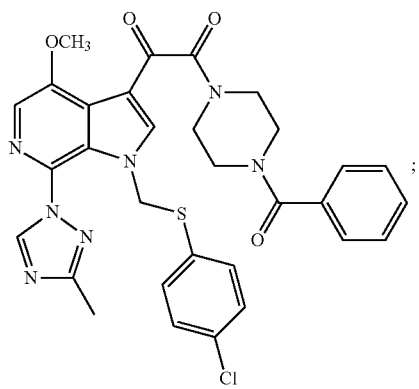

and (l) then converting the compound 12 to the compound (13)

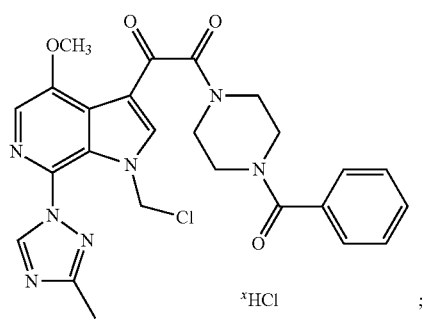

and (m) then reacting the compound 13 to produce the compound (14)

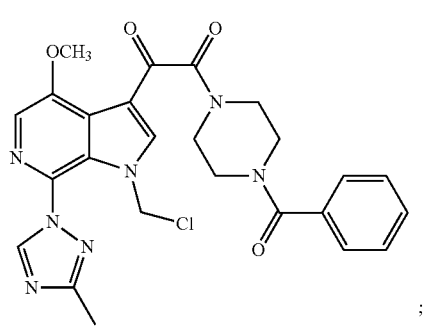

and (n) then reacting the compound 14 to produce the compound (15)

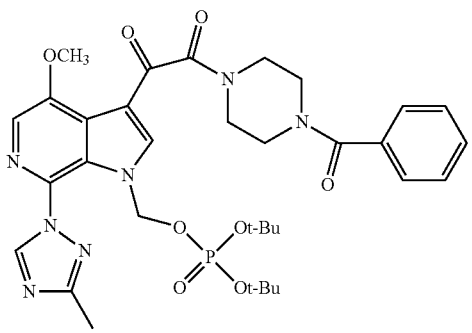

and (o) then converting the compound 15 to the compound of Formula I.

In a further embodiment of the invention, there is provided a method of making the compound of Formula I:

(I)

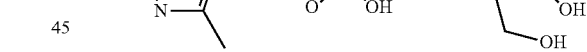

which comprises:

(i) reacting the compound (10)

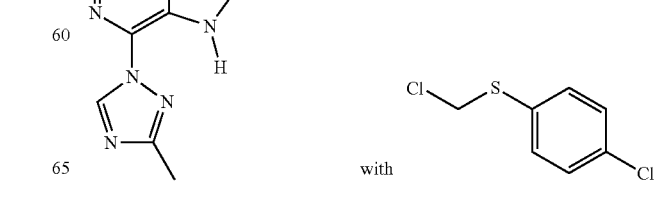

with

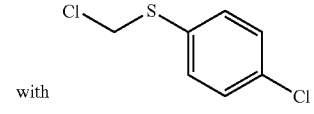

in the presence of TMG, NMP and NaI or $K_2CO_3$, MeCN and TBAI to yield the compound.

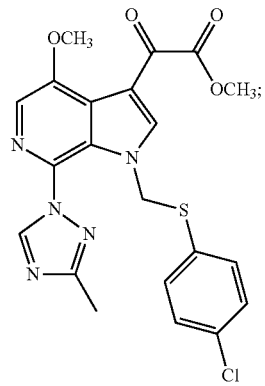
(11)

and
(ii) reacting compound 11 with

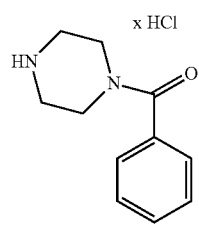

to produce the compound

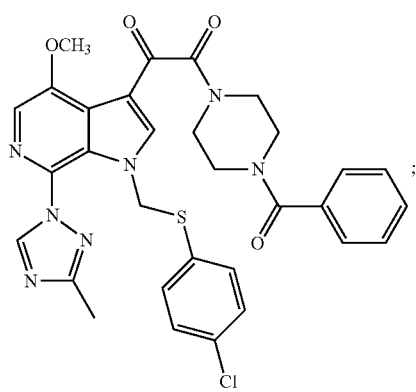
(12)

and
(iii) then converting the compound 12 to the compound

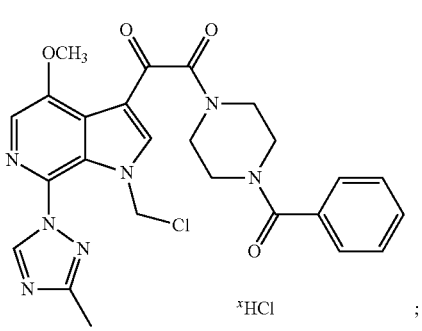
(13)

(iv) and then reacting compound 13 to produce

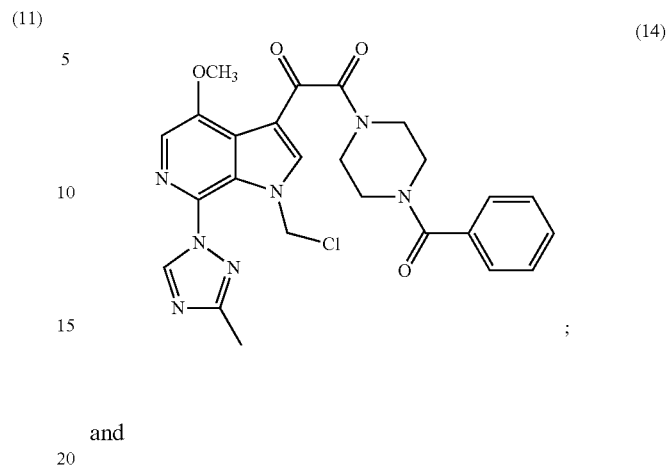
(14)

and (v) then reacting the compound 14 to produce the compound

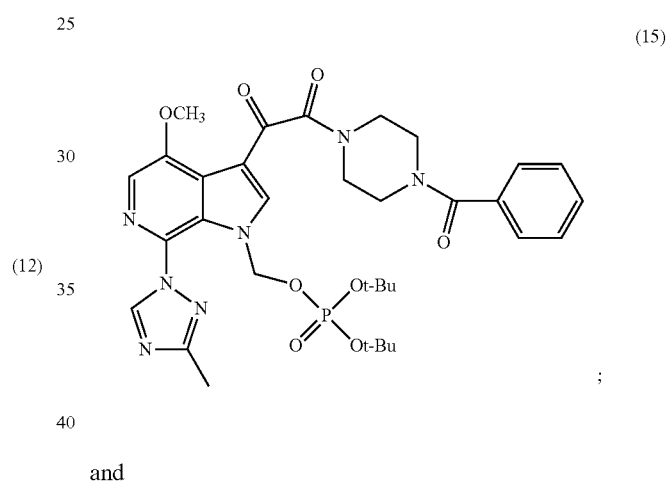
(15)

and then converting the compound 15 to the compound of Formula I.

Also provided herein is a method for making the compound of formula (14):

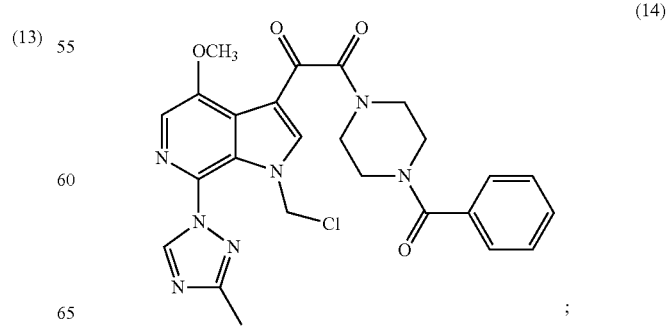
(14)

which comprises:

(i) reacting the compound

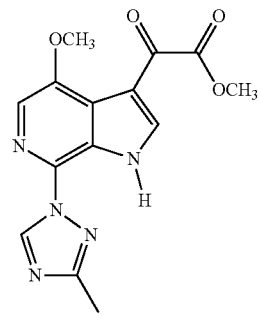

with 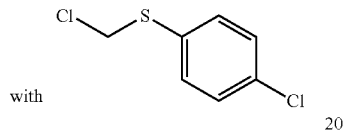

to yield the compound

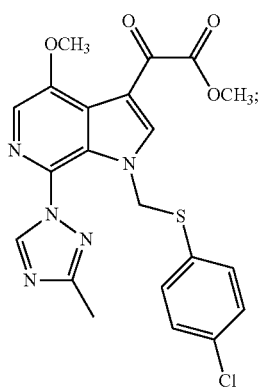

and (ii) reacting compound 11 to produce the compound

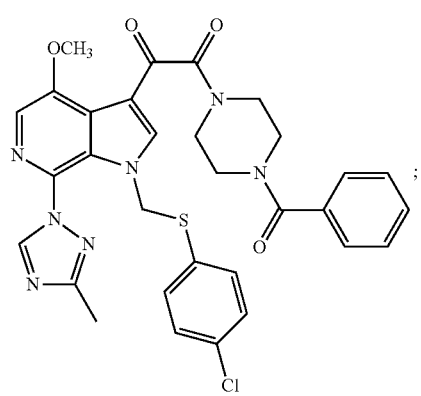

and (iii) then converting the compound 12 to the compound

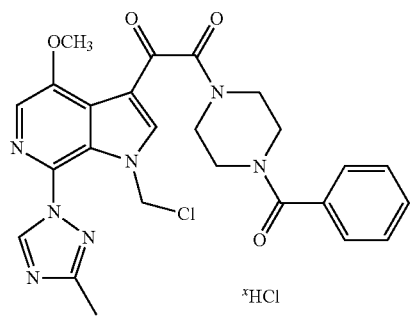

$^{x}$HCl ;

(iv) and then converting compound (13) to the compound

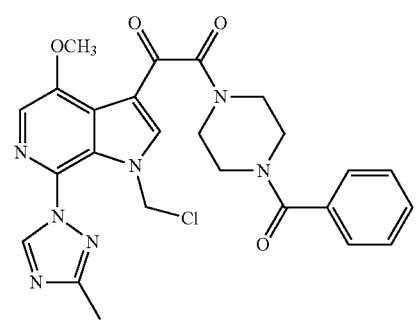

The invention is also directed to the more general chemical transformation of converting a thio ether to the corresponding chloride using a chlorinating agent.

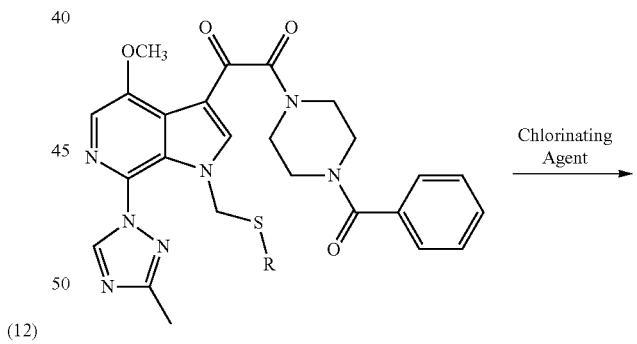

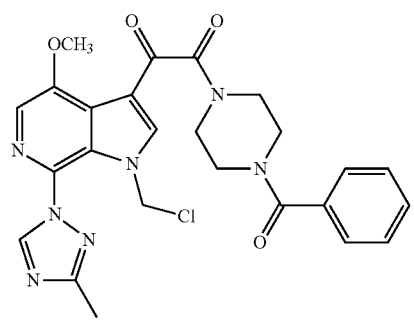

(14)

wherein R can be, but is not limited to alkyl, cycloalkyl, phenyl, substituted and polysubstituted phenyl rings, heteroaromatic rings, substituted and polysubstituted heteroaromatic rings. The chlorinating agent employed in this transformation can be, but is not limited to, chlorine gas, sulfuryl chloride, hexachloroethane, dichlorotriphenylphosphorane, N,N-dichloro-4-methylbenzenesulfonamide, trichloroisocyanuric acid, N-Chlorosuccinimide, 2-chloroisoindoline-1,3-dione or N-chlorosaccharin.

The invention is also directed to the novel compounds

The invention is directed to these and other important ends, hereinafter described.

DETAILED DESCRIPTION OF THE EMBODIMENTS

The invention provides methods for the production of the compound of Formula I:

as well as certain intermediates. The overall reaction scheme may be summarized and set forth as follows:

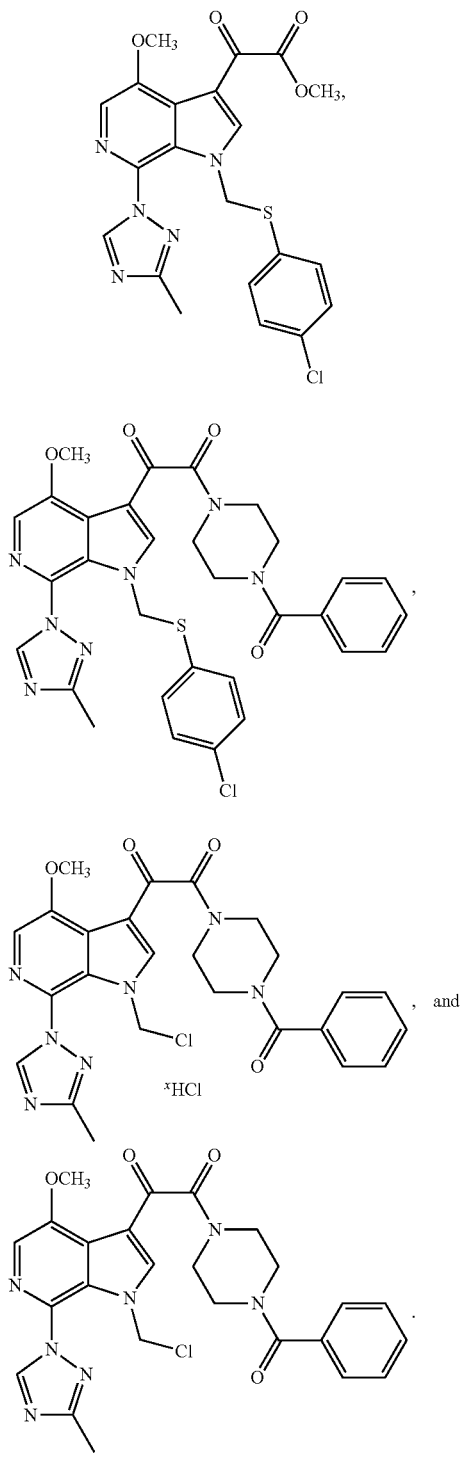

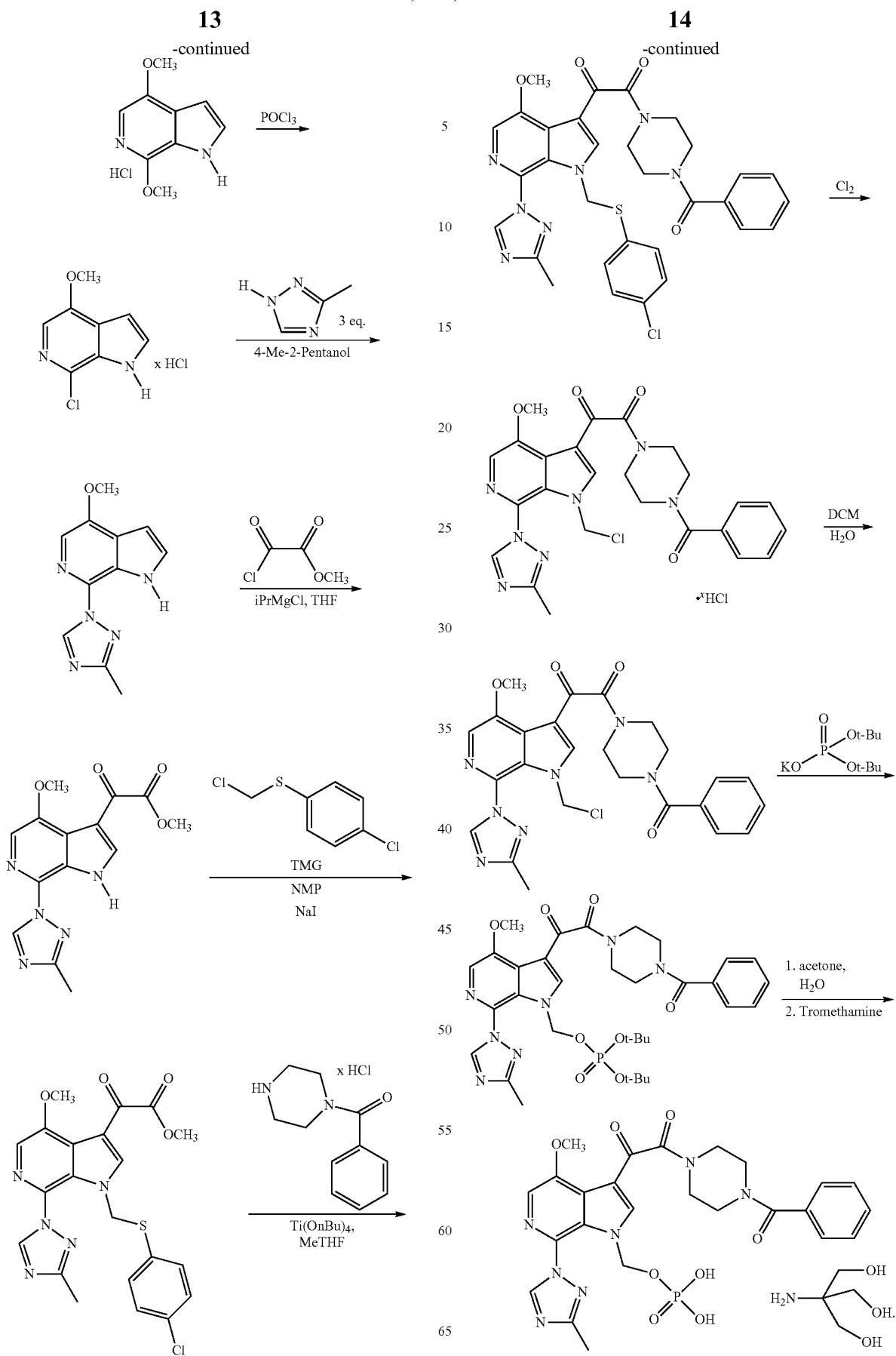

Thus, in a first embodiment the compound

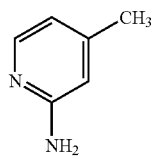

is utilized as starting material. This compound is reacted with acetic anhydride (Ac₂O) and then bromine to produce

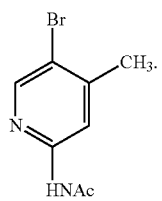

Next, this compound is reacted with nitric acid and sulfuric acid to produce

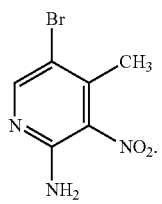

Thereafter, this compound is then reacted with sodium nitrite (NaNO₂) and trimethylsilyl chloride (TMS-Cl) in methanol (MeOH) to yield

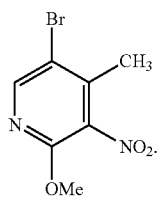

Then this compound is reacted with

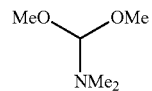

to produce

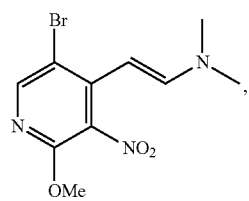 [SMILES: COc1ncc(Br)c(/C=C/N(C)C)c1[N+](=O)[O-]]

which is then reacted with a mixture of NaOMe/MeOH, CuI and NH₄Cl in tetrahydrofuran (THF) and methyl propionate to produce

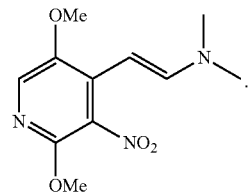 [SMILES: COc1cnc(OC)c([N+](=O)[O-])c1/C=C/N(C)C]

This compound is then reacted with 1% Pd/C under a hydrogen gas (H₂) atmosphere in ethyl acetate (EtOAc) to yield

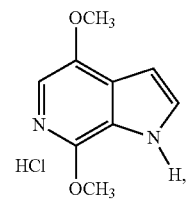

which is further reacted with POCl₃ to produce

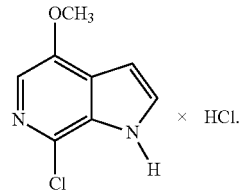

This resultant compound is in turn reacted with three (3) equivalents of

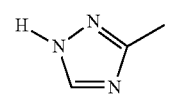

in 4-Me-2-pentanol to produce

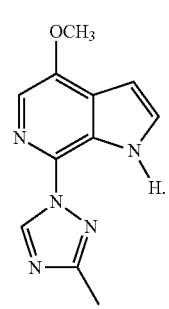

This compound is then reacted with

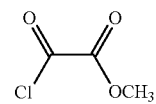

in iPrMgCl and THF to get

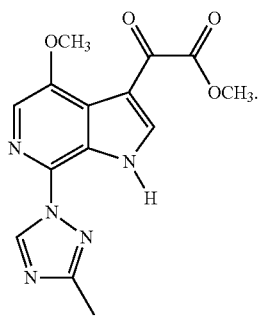 [SMILES: COC(=O)C(=O)c1c[nH]c2c(-n3cnc(C)n3)ncc(OC)c12]

Next, this compound is reacted with

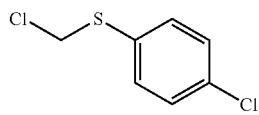

and tetramethylguanidine (TMG) in N-methylpyrrolidone (NMP) or $K_2CO_3$ in MeCN to obtain

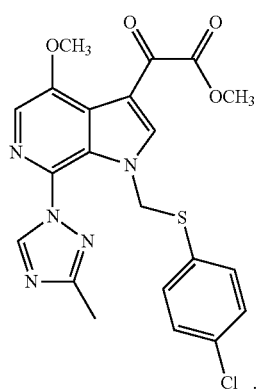

This compound is then reacted with

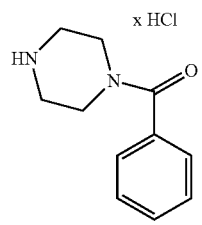 [SMILES: O=C(c1ccccc1)N1CCNCC1]

in $Ti(OnBu)_4$ and MeTHF to yield

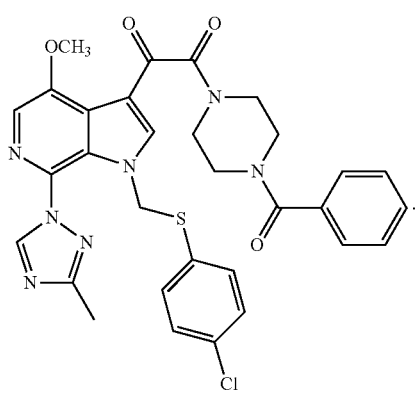 [SMILES: COc1cnc(-n2cnc(C)n2)c2c1c(C(=O)C(=O)N1CCN(C(=O)c3ccccc3)CC1)cn2CSc1ccc(Cl)cc1]

Next, this compound is chlorinated using chlorine gas ($Cl_2$) to yield

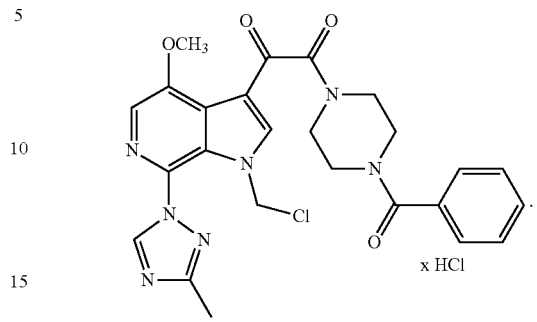

Next, this compound is reacted with dichloromethane (DCM) in water to produce

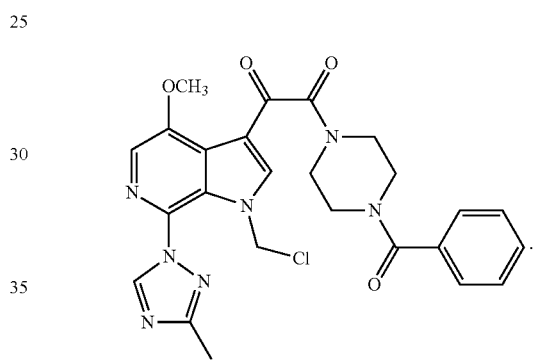

This compound is then further reacted with

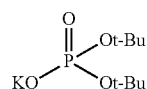

to obtain

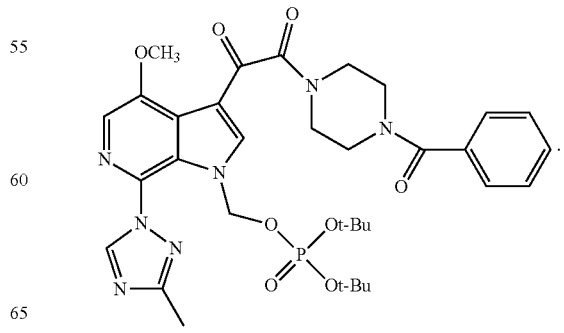

Finally, there is a further reaction with acetone in water, and then tromethamine to produce the prodrug

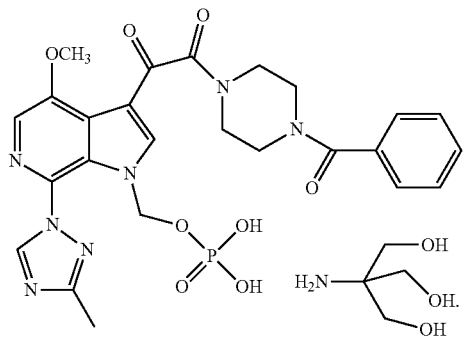

In a further embodiment of the invention, the compound of Formula I above is produced utilizing

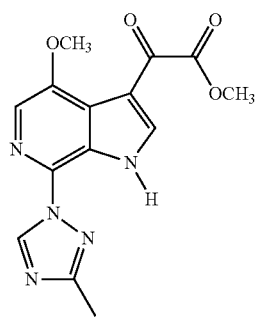 [SMILES: COC(=O)C(=O)c1c[nH]c2c(-n3cnc(C)n3)ncc(OC)c12]

as a starting material. This compound may be synthesized according to the procedures detailed above, or may be obtained according to the processes set forth and described in U.S. 20060293304, 28 Dec. 2006, which is incorporated herein by reference in its entirety.

In this embodiment,

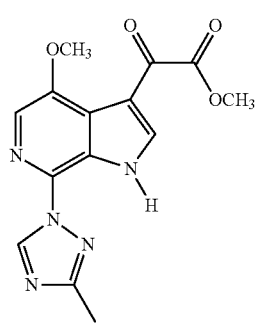 [SMILES: COC(=O)C(=O)c1c[nH]c2c(-n3cnc(C)n3)ncc(OC)c12]

is first reacted with

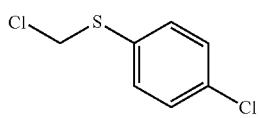

in the presence of TMG, NMP and NaI or $K_2CO_3$, MeCN and TBAI to yield the compound

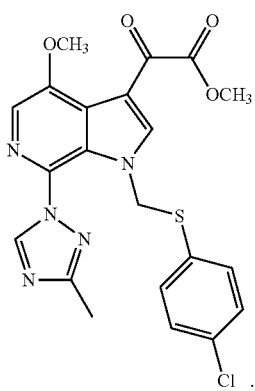

Next, this compound is reacted with

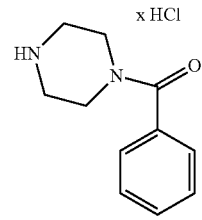 [SMILES: O=C(c1ccccc1)N1CCNCC1]

to produce the compound

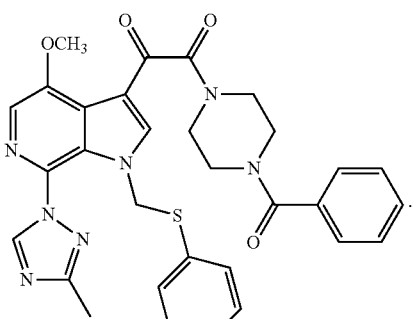

This compound is then converted to the compound

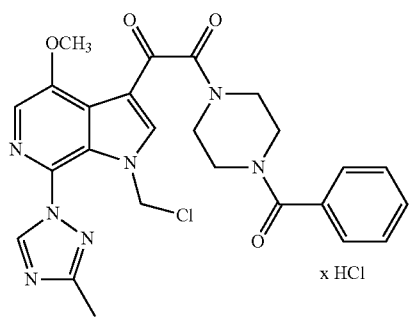 [SMILES: COc1cnc(-n2cnc(C)n2)c2c1c(C(=O)C(=O)N1CCN(C(=O)c3ccccc3)CC1)cn2CCl]

using chlorine (Cl$_2$) gas. Thereafter, this compound is converted to

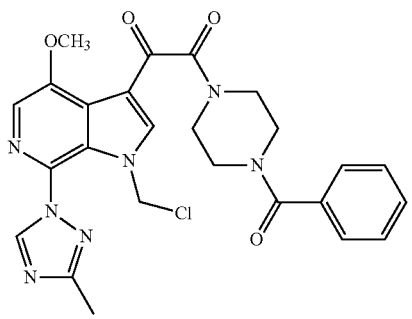 [SMILES: COc1cnc(-n2cnc(C)n2)c2c1c(C(=O)C(=O)N1CCN(C(=O)c3ccccc3)CC1)cn2CCl]

using dichloromethane in water. This compound is then reacted to produce the compound

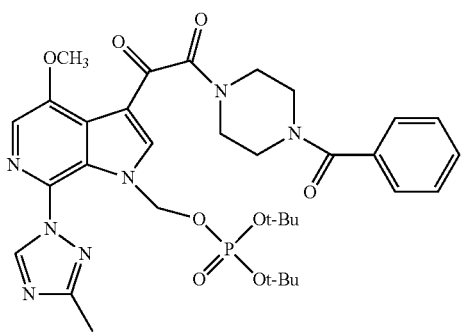 [SMILES: COc1cnc(-n2cnc(C)n2)c2c1c(C(=O)C(=O)N1CCN(C(=O)c3ccccc3)CC1)cn2COP(=O)(OC(C)(C)C)OC(C)(C)C]

using

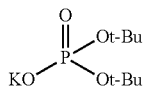

and finally, this compound is then converted to the compound of Formula I with acetone in water, and then tromethamine.

In a further embodiment of the invention, the compound of formula (14) is made using the compound of formula (10) as starting material. This process involves reacting the compound

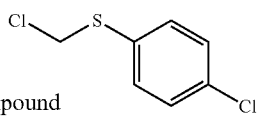

to yield the compound

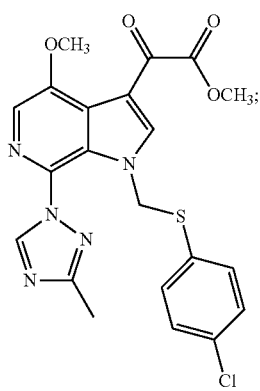

(11)

and then reacting compound 11 to produce the compound

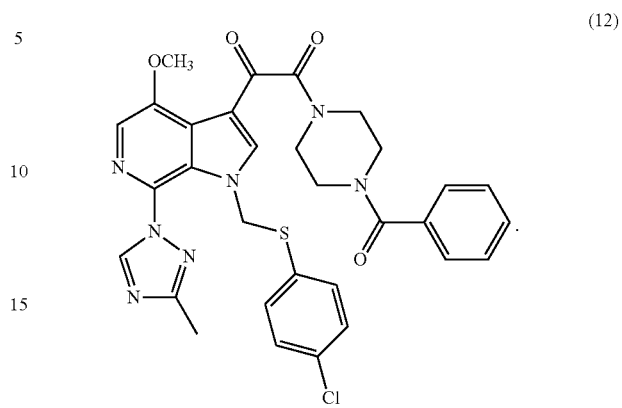

(12)

Next, compound 12 is converted to the compound

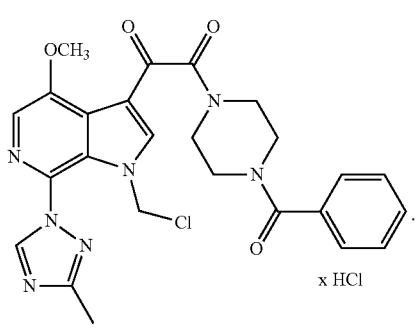

(13)

Thereafter, compound 13 is converted to the compound

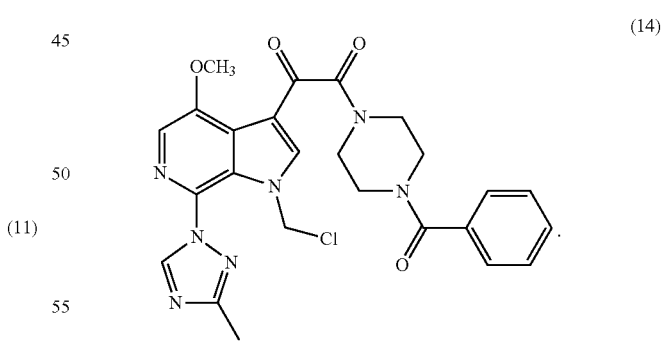

(14)

Compounds 11, 12, 13 and 14 thus constitute further embodiments of the invention.

The following Example sets forth a preferred method of the invention, but should not be construed as limiting the scope thereof:

EXAMPLE

In this Example, the compound

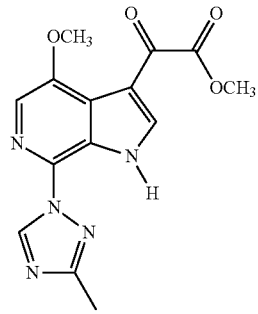

(10)

was used as the starting material. (see U.S. 20060293304, 28 Dec. 2006 for producing Compound 10). Below is the summary of the procedure for converting compound 10 to compound 11:

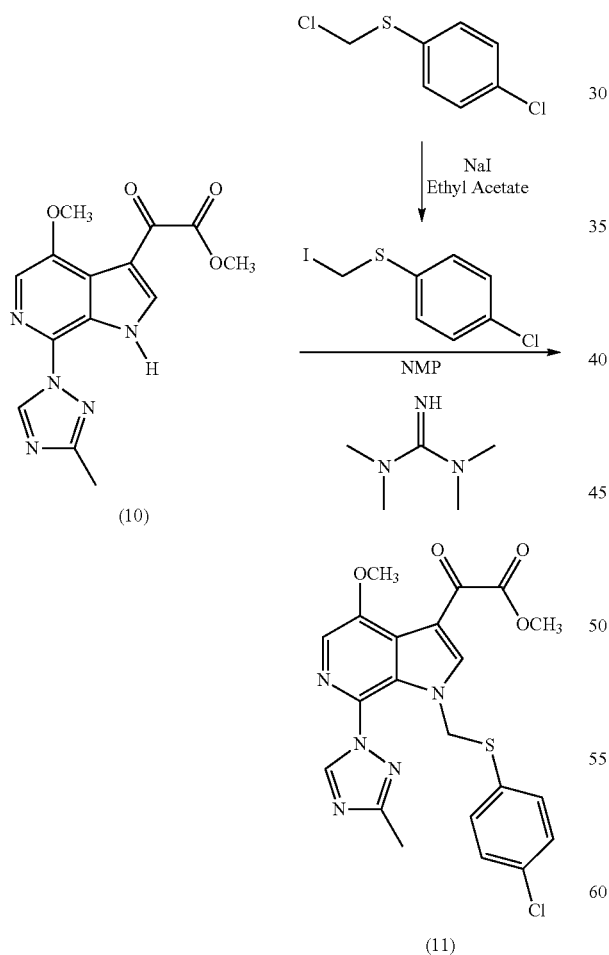

A 20 L and a 10 L reaction vessel were purged with inert gas. All steps were performed under inert gas protection.

To the 20 L reactor was charged 1.80 L of ethyl acetate at room temperature. To this was added 0.48 kg of the compound

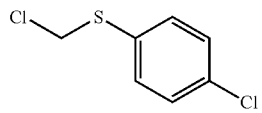

To this solution was added 0.34 kg of sodium iodide. All glassware used in the additions was then washed with 0.45 L of ethyl acetate which was also charged to the 20 L reactor.

The reaction mixture was heated to 65° C. internal temperature and agitated at this temperature for 3 hours.

A sample of the reaction mixture was analyzed by $^1$H NMR to determine conversion of

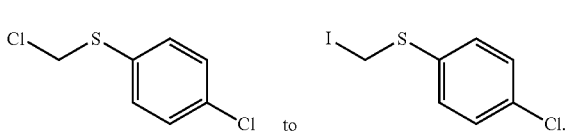 [SMILES: ClCSc1ccc(Cl)cc1 ; Clc1ccc(SCI)cc1]

If conversion is not greater than 90%, heating is continued.

Upon completion, the solution of

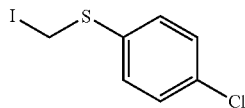

was allowed to cool to room temperature.

To a 10 L vessel is added 1.58 L of N-Methylpyrrolidinone (NMP) followed 0.18 kg of N,N,N',N'-tetramethylguanidine (TMG). To this solution was charged 0.45 kg of the compound 10. Finally all of the glassware used for the additions was rinsed with 0.50 L of NMP.

The mixture was agitated at room temperature for 2 hours. The NMP solution in the 10 L reactor was then transferred to the EtOAc solution of

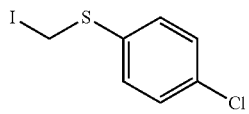

over 1 hour. The flask was then rinsed with 0.18 L of NMP which was also added to the solution of

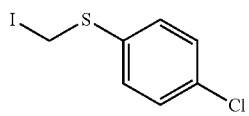

over 2 minutes.

The resulting mixture was agitated at room temperature for 1 hour.

A sample of the reaction mixture was taken for high pressure liquid chromatography (HPLC) monitoring.

To the reaction was added a total of 0.099 kg of TMG in 10 equal portions over 2 hours and the resulting mixture was agitated at room temperature for 14 hours.

A sample of the reaction mixture was taken HPLC monitoring.

To the reaction was charged 6.75 L of EtOAc followed by 4.50 L of 0.5 N aqueous hydrochloric acid solution (HCl). The mixture was vigorously agitated for 30 minutes and then the phases were allowed to settle and the bottom phase was discarded.

To the remaining upper phase was added 2.50 L of EtOAc, followed by the slow addition of 4.50 L of 0.5N HCl. The biphasic mixture was agitated vigorously for 15 minutes and then the phases were allowed to settle and the bottom phase was discarded.

To the remaining upper phase was added 0.50 L of EtOAc, followed by the slow addition of 4.50 L of 0.5N HCl. The biphasic mixture was agitated vigorously for 15 minutes and then the phases were allowed to settle and the bottom phase was discarded.

To the remaining upper phase was added 1.10 L of EtOAc followed by 4.50 L of distilled water. The biphasic mixture was agitated vigorously for 15 minutes and then the phases were allowed to settle and the bottom phase was discarded.

To the remaining upper phase was added 0.5 L of EtOAc followed by 4.50 L of distilled water. The biphasic mixture was agitated vigorously for 15 minutes and then the phases were allowed to settle and the bottom phase was discarded.

The final organic stream was gradually transferred to a 10 L reactor in 4.00 L increments with a 1.00 L EtOAc wash of the 20 L reactor and between each charge the volume of the stream was reduced to 3.60 L by distillation of the solvent.

The solvent composition was then changed from primarily EtOAc to primarily isopropyl alcohol (IPA) using a put and take distillation with a total of 9.00 L of IPA and never allowing the total reaction volume to fall below 3.60 L. The final solution was allowed to age for 8 hours.

The resulting slurry was filtered in order to isolate the product. The product was then washed twice with 1.12 L of IPA. The isolated product was dried at a maximum temperature of 50° C. until reaching a constant weight. The yield was 0.43 kg (63.23%) of compound 11 as beige crystals.

Analytical data: m.p. 127.0-128.8° C. $^1$H-NMR (Acetic Acid, $d_4$) ($\delta$, ppm): 9.01 (s, 1H), 8.06 (s, 1H), 7.93 (s, 1H), 7.25 (d, J=8.5 Hz, 2H), 7.07 (d, J=8.5 Hz, 2H), 5.60 (s, 2H), 4.10 (s, 3H), 3.95 (s, 3H), 2.58 (s, 3H). $^{13}$C-NMR (Acetic Acid, $d_4$) ($\delta$, ppm): 181.4, 165.1, 162.0, 152.1, 147.4, 142.7, 136.3 (3C), 130.6, 130.4 (2C), 129.9, 127.9, 126.8, 122.8, 114.3, 57.3, 56.7, 53.3, 13.3. HRMS: Calcd for $C_{21}H_{19}O_4N_5ClS$ [M+1]$^+$ 472.0841 found 472.0841. Elemental Analysis: C, 53.44; H, 3.84; N, 14.84, S, 6.79, Cl, 7.51. found: C, 53.53; H, 3.55; N, 14.63, S, 6.98, Cl, 7.73.

The process was then continued as follows, with a summary of the conversion of compound 11 to compound 12 set forth below:

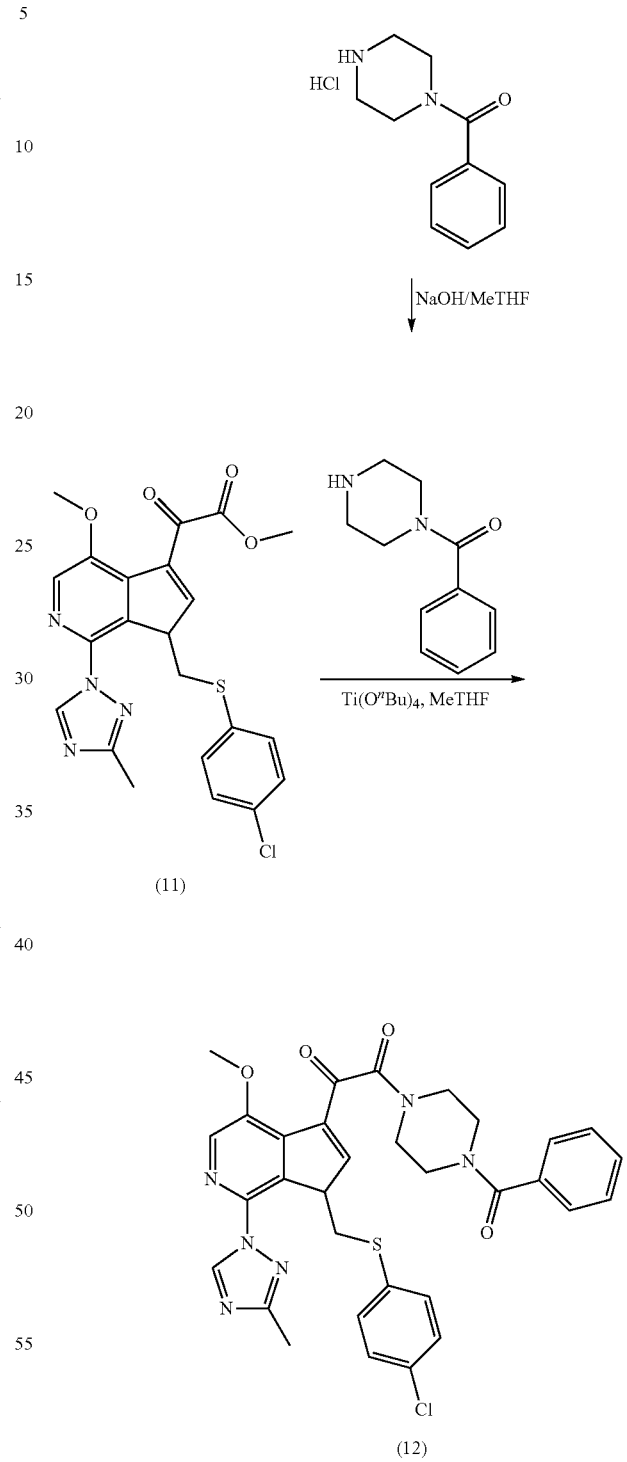

A reaction vessel was purged with inert gas. All steps were performed under inert gas protection.

The vessel was then charged with 8.0 L of MeTHF at 20-25° C. Next, charged 800 g of compound

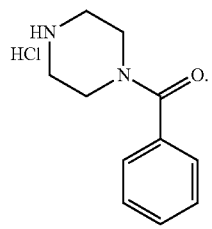

A white slurry forms. To the slurry was charged 488 ml of water and 388 ml of 1 N NaOH. No exotherm was observed.

Agitation was removed after 1 hour and the layers were allowed to settle. The bottom aqueous layer was removed. The remaining organic layer was heated to reflux and approximately 3 L of MeTHF was distilled. At this point the distillation was performed under constant volume conditions When a KF of <500 ppm was obtained the mixture was allowed to cool to room temperature. The organic layer was filtered and the concentration of benzoyl piperazine was measured.

A separate vessel was purged with inert gas.

To the vessel was charged 5.2 L of the above solution of the compound

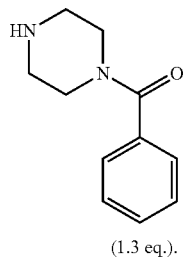

(1.3 eq.).

This was followed by the addition of 1 kg of compound 11 was charged resulting in a white slurry. Finally, 260 ml of Ti(O"Bu)$_4$ and 800 ml of MeTHF were charged.

The mixture was heated to reflux. After 3 hours the mixture was seeded with 2 g of the compound of formula 11. The reaction was allowed to continue to reflux.

Upon completion, the slurry was cooled to 10° C. and allowed to agitate for 2 hours. The product was filtered, washed with 2 L of MeTHF then 3.15 L of EtOH. The product was dried at 50° C. in a vacuum oven until reaching a constant weight. The yield was 1.07 kg (80.4%) of off white crystals of compound of formula 12.

Analytical Data: m.p. 162° C. $^1$H-NMR (CDCl$_3$) (δ, ppm): 2.54 (s, 3H), 3.52 (bs, 4H), 3.74 (bs, 4H), 4.08 (s, 3H), 5.52 (s, 2H), 6.96 (d, J=8.2 Hz, 2H), 7.2 (d, J=8.8 Hz, 2H), 7.44 (bs, 5H), 7.62 (s, 1H), 7.91 (s, 1H), 8.62 (s, 1H): $^{13}$C-NMR (CDCl$_3$) (δ, ppm): 13.91, 41.6, 45.9, 56.5, 56.8, 114.3, 122.3, 125.1, 126.7, 127.0, 128.64, 129.5, 129.6, 129.8, 130.2, 134.9, 135.2, 135.7, 140.8, 145.5, 150.6, 161.9, 165.9, 170.6, 184.4; HRMS; cacld for C$_{31}$H$_{29}$ClN$_7$O$_4$S [M+1]$^+$: 630.1685; found: 630.1688. Elemental Analysis: C, 59.09; H, 4.47; N, 15.56, S, 5.08, Cl, 5.62. found: C, 59.05; H, 4.28; N, 15.57, S, 5.07, Cl, 5.66.

The process was then continued as follows, with a summary of the process for the conversion of compound 12 to compound 14 set forth below:

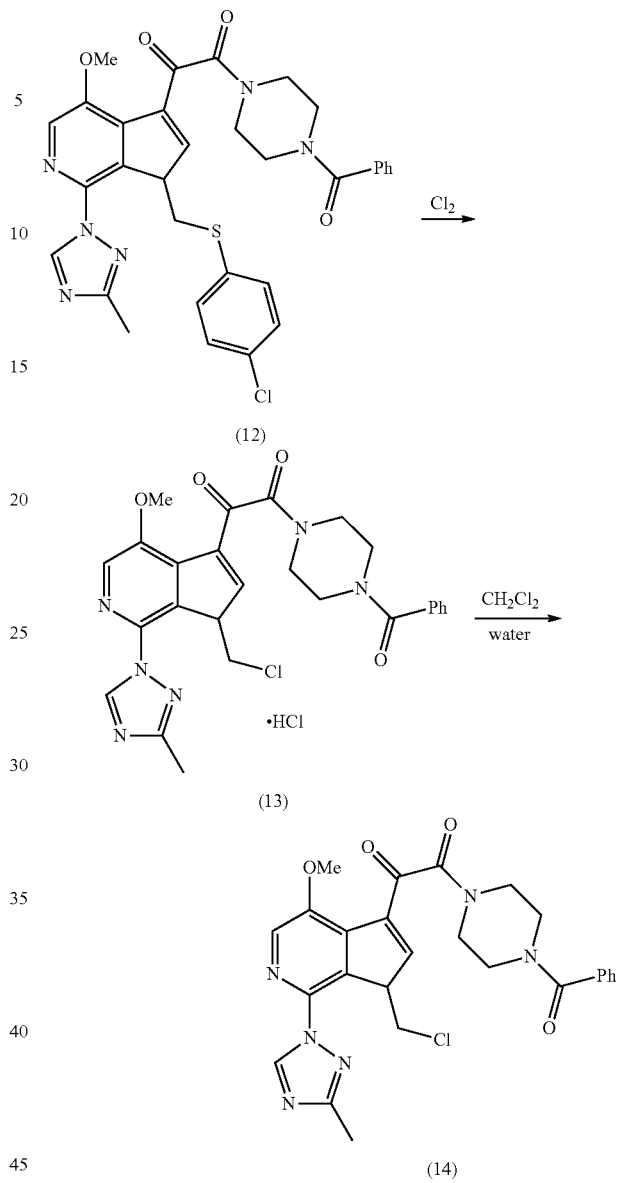

A reaction vessel was purged with inert gas. All steps were performed under inert gas protection.

The vessel was then charged with 5 L of dichloromethane at 20-25° C. Next, 1.00 kg of the compound of formula 12 was added to the vessel to produce a colorless solution. The solution was then cooled to 0° C. (−3 to 3° C.), followed by the subsurface addition of 113 g chlorine. An orange solution was formed and the reaction was noted to be exothermic. The temperature was kept near 0° C. (−3 to 3° C.).

A sample was taken for high pressure liquid chromatography (HPLC) monitoring, and additional chlorine charges were added as necessary.

Upon reaction completion, solution was warmed to 15° C.

A solution of isopropanol (1.0 eq.) and 10 L of acetone were prepared. 5 vol % of this solution was added to the vessel over about 30 minutes to produce a thin yellow suspension. After a 30 min age, the remaining 95 vol % of the isopropanol/acetone solution was added over 2 h to produce a white suspension. This addition was slightly exothermic and some cooling was necessary ($T_{max}$=25° C.). Slurry was aged at 20° C. and HPLC was utilized to monitor the crystallization progress.

Product 13 was then filtered, and washed with 5 L of 2:1 (v:v) acetone:dichloromethane, followed by 2.5 L of acetone.

Product 13 could then either be dried at a maximum temperature of 50° C. until reaching constant weight or the wet cake taken forward to product 3.

For the isolation of 13, yield was 0.78 kg (88%) as white crystals.

For the isolation of 14, a second reaction vessel was purged with inert gas.

The vessel was then charged with 5 L of dichloromethane at 20-25° C. Next, about 1.10 kg of the wet cake compound of formula 13a was added to the vessel to produce a white suspension, followed by the addition of 5 L water. A biphasic solution formed and the temperature was kept near 22° C. (20 to 25° C.).

A phase-split was conducted, and the lower, product-rich organic layer was then charged with 1.5 L ethyl acetate under constant-volume distillation conditions (pressure=400 mbar). The resulting solution was then seeded with 13b, and aged for 30 min. 9-12 L of additional ethyl acetate were then added under constant-volume distillation conditions (pressure down to <100 mbar).

Slurry was aged at 20° C. and HPLC was utilized to monitor the crystallization progress.

Product 14 was then filtered, and washed with 4 L of ethyl acetate.

Product 14 was then dried at a maximum temperature of 50° C. until reaching constant weight.

For the isolation of 14, yield was 0.70 kg (85%) as white crystals.

Analytical data for 13: m.p. 121° C. $^1$H-NMR (d7-DMF) (δ, ppm): 11.17 (br s, 1H), 9.18 (s, 1H), 8.88 (s, 1H), 8.19 (s, 1H), 7.52-7.54 (m, 5H), 6.44 (s, 2H), 4.19 (s, 3H), 3.67-3.84 (m, 8H), 2.55 (s, 3H); $^{13}$C-NMR (d7-DMF) (δ, ppm): 185.4, 169.9, 166.2, 161.3, 151.1, 146.6, 142.3, 136.1, 129.9, 129.5, 128.6, 127.3, 127.2, 124.7, 123.4, 116.1, 57.7, 56.9, 45.9, 41.7, 13.1; HRMS calcd for $C_{25}H_{25}ClH_7O_4$ [M-Cl]$^+$: 522.1578 found 522.1648. Elemental analysis: C, 53.77; H, 4.51; N, 17.55, Cl, 12.69. found: C, 53.05; H, 4.68; N, 17.20, Cl, 12.56.

Analytical data for 14: m.p. 211° C. $^1$H-NMR (CDCl$_3$) (δ, ppm): 8.59 (s, 1H), 8.14 (s, 1H), 7.91 (s, 1H), 7.41 (s, 5H), 6.09 (s, 2H), 4.04 (s, 3H), 3.40-4.00 (m, 8H), 2.51 (s, 3H); $^{13}$C-NMR (CDCl$_3$) (δ, ppm): 184.4, 170.6, 165.7, 162.1, 150.6, 145.6, 140.8, 134.8, 130.1, 129.6, 128.6, 127.0, 126.7, 125.1, 122.9, 116.1, 57.1, 56.8, 45.9, 41.7, 13.9; HRMS: calcd for $C_{25}H_{25}ClH_7O_4$ [M+H]$^+$:522.1578, found 522.1653. Elemental analysis: C, 57.52; H, 4.64; N, 18.78, Cl, 6.79. found C, 57.26; H, 4.60; N, 18.44, Cl 7.14.

The process was then continued as follows, with a summary of the process for the conversion of compound 14 to compound 15 set forth below:

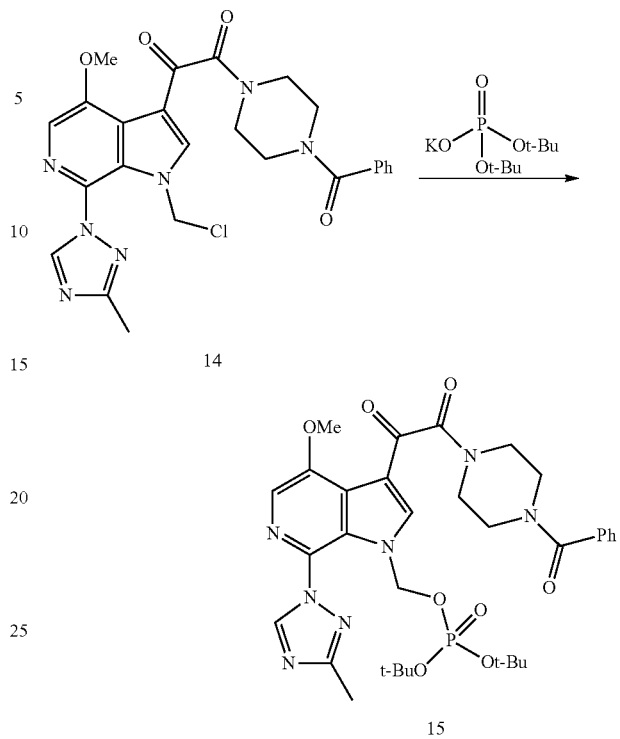

A reaction vessel was purged with inert gas. All steps were performed under inert gas protection.

The vessel was then charged with 3 L of dichloromethane at 20-25° C. Next, 1.00 kg of the compound of formula 14, 0.20 kg of tetraethylammonium bromide (0.50 eq.) and 0.5 L dichloromethane were added to the vessel to produce a colorless solution. The solution was then warmed to 35° C. (33 to 37° C.), and charged with 0.57 kg of di-tert-butyl potassium phosphate (1.2 eq.) in 4×0.3 eq. portions over 1 h, followed by 0.5 L dichloromethane. A yellow suspension formed and the reaction was warmed to 40° C. (38 to 42° C.).

A sample was taken for high pressure liquid chromatography (HPLC) monitoring, and additional di-tert-butyl potassium phosphate was added if necessary.

Upon reaction completion, suspension was cooled to 20° C.

The vessel was then charged with 5 L water and the resulting biphasic solution was kept near 20° C. (18 to 22° C.).

A phase-split was conducted, and the lower, product-rich organic layer was then charged with 5 L of 20:1 (v:v) tert-butylmethyl ether:isopropanol. The solution was then seeded with compound 15, and aged for 30 min. 11 L of additional 20:1 (v:v) tert-butylmethyl ether:isopropanol was then added over 3 h.

Slurry was aged at 20° C. and HPLC was utilized to monitor the crystallization progress.

Compound 15 was then filtered, and washed with 5 L of 4:1 (v:v) [20:1 (v:v) tert-butylmethyl ether:isopropanol]: dichloromethane, followed by 5 L of tert-butylmethyl ether.

Compound 15 was then dried at a maximum temperature of 50° C. until reaching constant weight.

For the isolation of compound 15, yield was 1.13 kg (85%) as white crystals.

Analytical data for 2: m.p. 198° C. $^1$H-NMR (CDCl$_3$) (δ, ppm): 8.51 (s, 3H), 8.17 (s, 3H), 7.88 (s, 3H), 7.39 (m, 5H), 5.92 (d, J=14 Hz, 2H), 4.03 (s, 3H), 3.30-3.80 (m, 8H), 2.47 (s, 3H), 1.25 (s, 18H); $^{13}$C-NMR (CDCl$_3$) (δ, ppm): 184.6, 170.5, 166.8, 161.4, 150.7, 145.3, 141.8, 134.9, 130.1, 129.5, 128.5, 127.5, 127.0, 124.6, 122.6, 115.1, 83.7 (d, J=7.4 Hz), 73.55 (d, J=6.6 Hz), 56.8, 45.9, 41.6, 29.5 (d, J=4.4 Hz), 13.8; $^{31}$P-NMR (CDCl$_3$) (δ, ppm): −10.0; HRMS: calcd for C33H43N7O8P [M+H]$^+$: 696.2832 found 696.2885. Elemental analysis: C, 56.97; H, 6.08; N, 14.09. found C, 57.00; H, 6.04; N, 14.13.

The above process may then be continued as herein set forth in the description to yield the compound of Formula I.

The compound of Formula I, once synthesized, may be utilized in compositions to treat HIV infection as set forth and described in U.S. Pat. Nos. 7,745,625, 7,354,924 and 7,776,863, by way of non-limiting examples.

The foregoing description is merely illustrative and should not be understood to limit the scope or underlying principles of the invention in any way. Indeed, various modifications of the invention, in addition to those shown and described herein, will become apparent to those skilled in the art from the following examples and the foregoing description. Such modifications are also intended to fall within the scope of the appended claims.

What is claimed is:

1. A method for making the compound of Formula I:

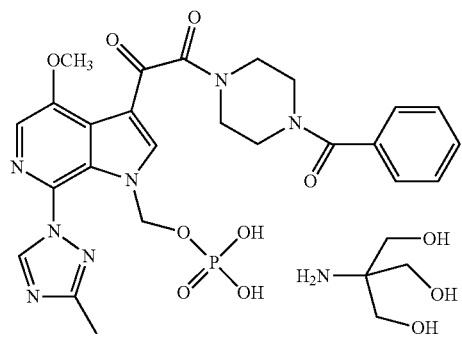

(I)

which comprises:

(a) brominating the compound

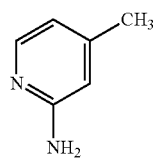

(1)

to yield the compound

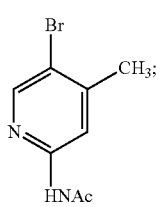

(2)

and (b) nitrating compound 2 to yield the compound

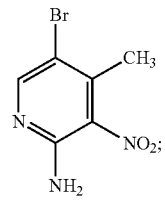

(3)

and (c) converting the amine group on compound 3 to a methoxy group to yield compound (4)

Br
CH$_3$
N
NO$_2$;
OMe and (d) then converting compound 4 to the compound

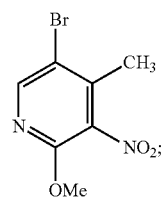

(5)

and (e) converting compound 5 to the compound (6)

OCH$_3$
N
N
NO$_2$
OMe and (f) forming a bicyclic structure from compound 6 to yield (7)

OCH$_3$
N
N
HCl  H;
OCH$_3$ and
(g) then chlorinating compound 7 to produce
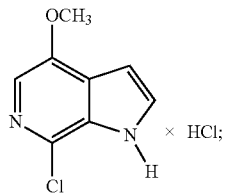
(8)
and
(h) thereafter adding a triazolyl moiety to the compound 8 to yield
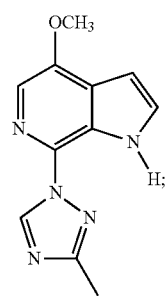
(9)
and
(i) converting compound 9 to the structure
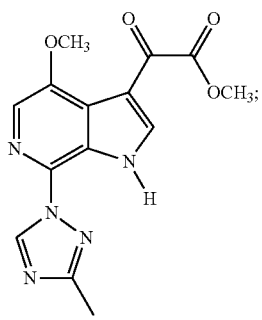
(10)
and
(j) modifying compound 10 to yield the compound
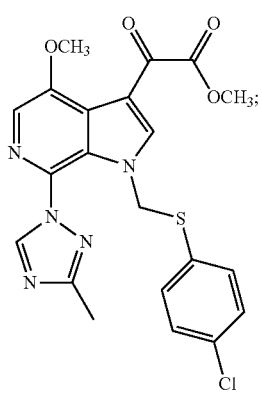
(11)
and
(k) reacting compound 11 to produce the compound
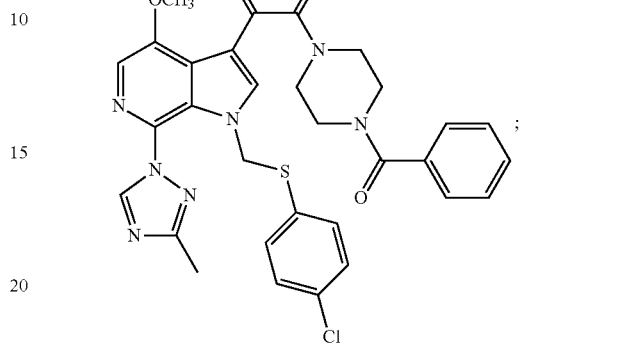
(12)
and
(l) then converting the compound 12 to the compound
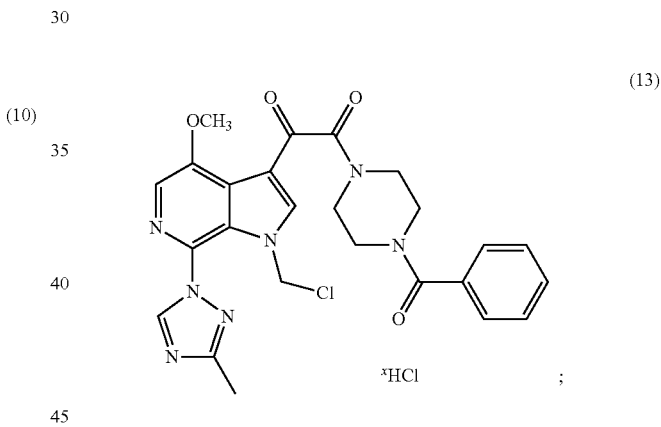
(13)
(m) then converting compound 13 to the compound
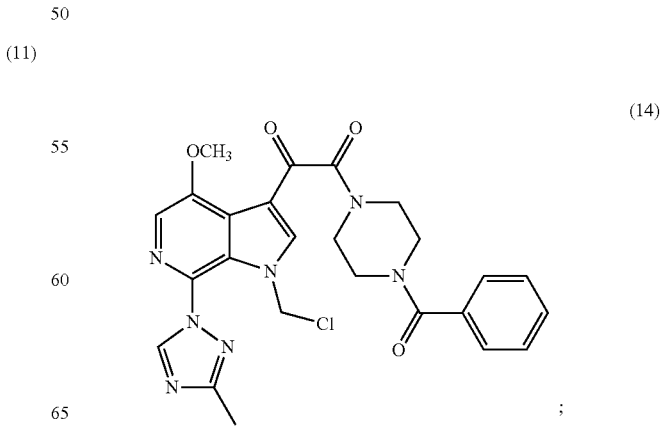
(14)

and
(n) then reacting the compound 14 to produce the compound

(15)
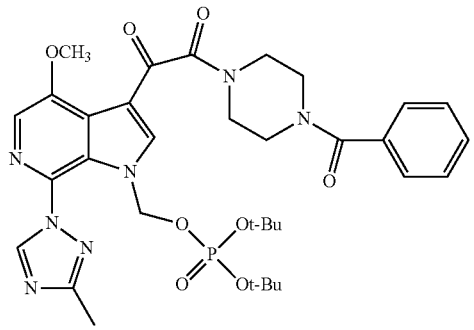

and
(o) then converting the compound 15 to the compound of Formula I.

2. A method for making the compound of Formula I:

(I)
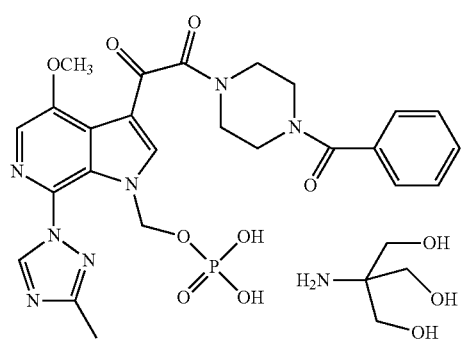

which comprises:
(i) reacting the compound

(10)
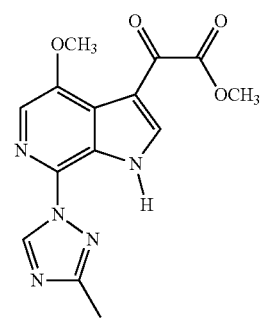

with

in the presence of TMG, NMP and NaI or $K_2CO_3$ and MeCN to yield the compound

(11)
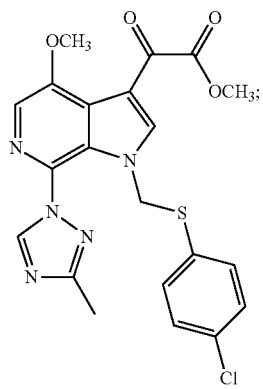

and
(ii) reacting compound 11 with

to produce the compound

(12)
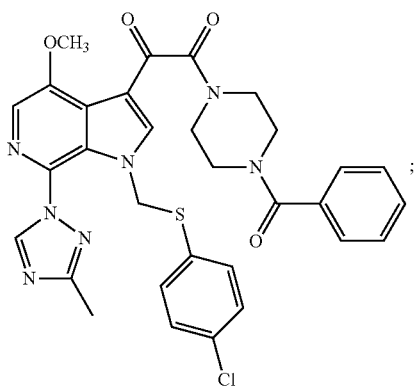

and
(iii) then converting the compound 12 to the compound

(13)
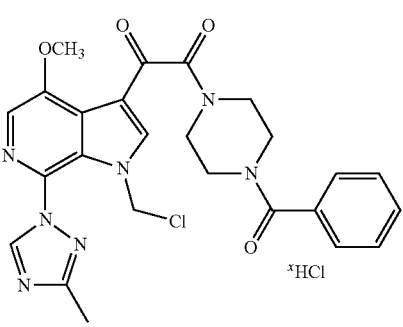

(iv) then converting the compound 13 to the compound (14)

and (v) then reacting the compound 14 to produce the compound (15)

and (vi) then converting the compound 15 to the compound of Formula I.

3. The method of claim 1, wherein step (a) is performed using Ac$_2$O.

4. The method of claim 1, wherein step (b) is performed under acidic conditions.

5. The method of claim 4, wherein step (b) is performed using nitric acid.

6. The method of claim 5, wherein step (b) is performed using nitric acid and sulfuric acid.

7. The method of claim 1, wherein step (c) is performed using NaNO$_2$ and TMS-Cl in alcohol.

8. The method of claim 7, wherein said alcohol is methanol.

9. The method of claim 1, wherein step (d) is performed using

10. The method of claim 1, wherein step (h) is performed using

11. The method of claim 1, wherein step (i) is performed using

12. The method of claim 1, wherein step (j) is performed using

13. The method of claim 2, wherein step (ii) is performed using

14. The method of claim 2, wherein step (iv) is performed using dichloromethane.

15. The method of claim 2, wherein step (v) is performed using

16. The method of claim 2, wherein step (vi) is performed using acetone in water and tromethamine.

17. A method for making the compound of formula (14):

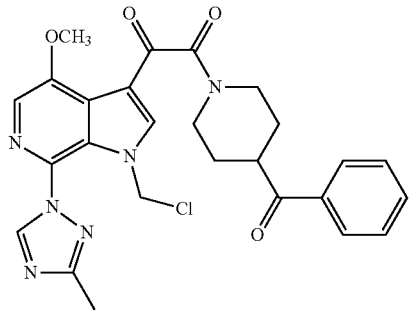
(14)

which comprises:
(i) reacting the compound

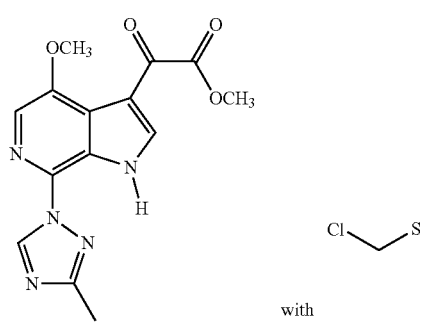
(10)

with

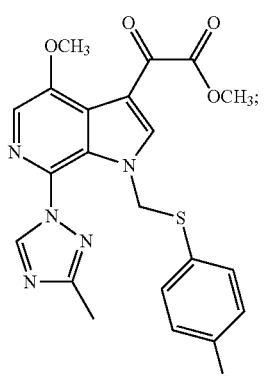

to yield the compound

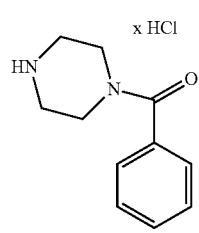 [SMILES: O=C(c1ccccc1)N1CCNCC1]
(11)

and
(ii) reacting compound 11 with

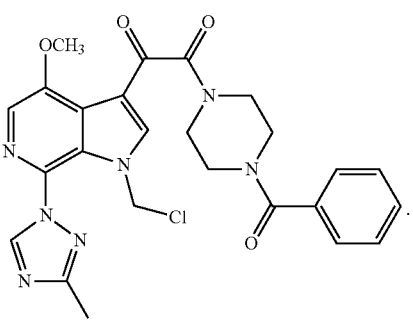
x HCl to produce the compound

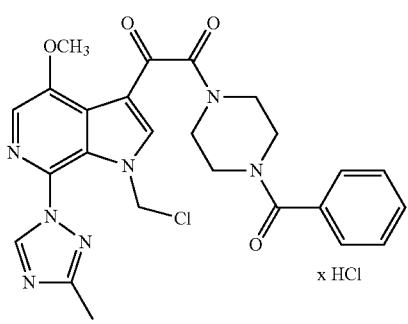
(12)

and (iii) then converting the compound 12 to the compound (13)

using chlorine gas;

(iv) then producing the compound 14

(14)

using dichloromethane.

18. The compound having the following formula:
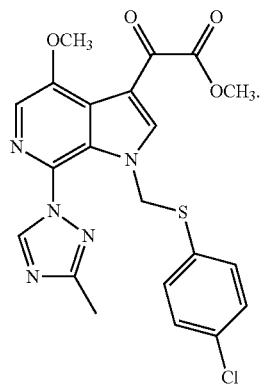 [SMILES: COC(=O)C(=O)c1cn(CSc2ccc(Cl)cc2)c2c(-n3cnc(C)n3)ncc(OC)c12]
19. The compound having the following formula:
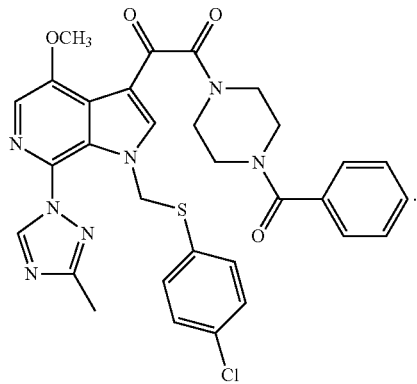 [SMILES: COc1cnc(-n2cnc(C)n2)c2c1c(C(=O)C(=O)N1CCN(C(=O)c3ccccc3)CC1)cn2CSc1ccc(Cl)cc1]
20. The compound having the following formula:
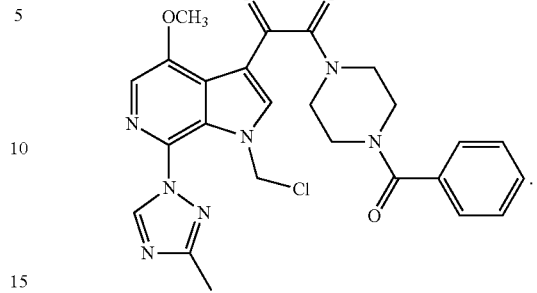
21. The compound having the following formula:
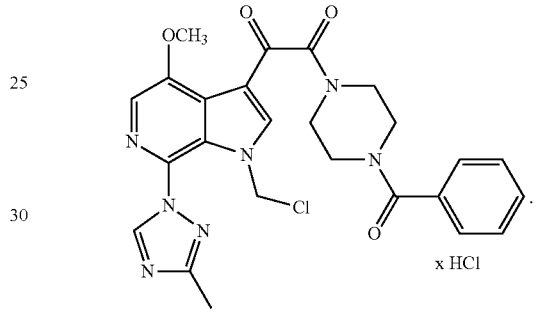
* * * * *